(12) United States Patent
Jen et al.

(10) Patent No.: US 11,812,930 B2
(45) Date of Patent: Nov. 14, 2023

(54) DEVICES FOR THE TREATMENT OF BENIGN PROSTATIC HYPERPLASIA AND RELATED LOWER URINARY TRACT SYMPTOMS

(71) Applicant: Prodeon Medical Corporation, Taipei (TW)

(72) Inventors: Jimmy Jen, Saratoga, CA (US); Dan Zaretzka, Sunnyvale, CA (US); Kenneth Chih-Ping Chang, San Jose, CA (US); Kondapavulur T. Venkateswara-Rao, San Jose, CA (US)

(73) Assignee: Prodeon Medical Corporation, Taipei (TW)

( * ) Notice: Subject to any disclaimer, the term of this patent is extended or adjusted under 35 U.S.C. 154(b) by 112 days.

(21) Appl. No.: 17/109,814

(22) Filed: Dec. 2, 2020

(65) Prior Publication Data

US 2021/0161642 A1    Jun. 3, 2021

Related U.S. Application Data

(60) Provisional application No. 62/943,112, filed on Dec. 3, 2019.

(51) Int. Cl.
*A61F 2/04* (2013.01)
*A61F 2/966* (2013.01)
(Continued)

(52) U.S. Cl.
CPC ........ *A61B 1/00135* (2013.01); *A61B 1/0008* (2013.01); *A61B 1/307* (2013.01);
(Continued)

(58) Field of Classification Search
CPC ...... A61F 2/04; A61F 2/966; A61F 2002/047; A61F 2220/0008; A61F 2/82;
(Continued)

(56) References Cited

U.S. PATENT DOCUMENTS 3,687,142 A * 8/1972 Leibinzohn ....... A61M 25/0108
600/433
4,762,128 A    8/1988 Rosenbluth
(Continued)

FOREIGN PATENT DOCUMENTS

CA         2017327       * 11/1990
EP         4101404 A2    * 12/2022 ......... A61B 17/3468
WO    WO2003045275 A3   * 6/2003  ......... A61B 17/3468

OTHER PUBLICATIONS

International Search Report and Written Opinion in corresponding International Patent Application No. PCT/US20/62860, dated Mar. 4, 2020.
(Continued)

*Primary Examiner* — Paul B Prebilic
(74) *Attorney, Agent, or Firm* — Dergosits & Noah LLP; Todd A. Noah

(57) ABSTRACT

Devices and methods are disclosed for managing and/or treating body tissues obstructing a hollow body lumen, including the prostatic lobe tissues obstructing the urethra, for example conditions including benign prostatic hyperplasia (BPH), bladder outlet obstruction (BOO), benign prostatic obstruction (BPO) and associated lower urinary tract symptoms (LUTS). A retrieval sheath having an elongated shaft member with at least one region of modified flexibility that is configured compress the implant to a reduced profile for removal from the patient's body.

19 Claims, 4 Drawing Sheets

(51) Int. Cl.
  *A61B 1/307* (2006.01)
  *A61B 1/00* (2006.01)
(52) U.S. Cl.
  CPC ............... *A61F 2/04* (2013.01); *A61F 2/966* (2013.01); *A61F 2002/047* (2013.01); *A61F 2220/0008* (2013.01)
(58) Field of Classification Search
  CPC ....... A61F 2002/825; A61F 2002/9528; A61B 1/0008; A61B 1/307
  See application file for complete search history.

(56) References Cited

U.S. PATENT DOCUMENTS

| | | |
|---|---|---|
| 8,631,831 B2 | 1/2014 | Dimalanta, Jr. et al. |
| 2002/0161425 A1* | 10/2002 | Hemerick ............... A61F 2/966 623/1.11 |
| 2003/0069647 A1 | 4/2003 | Desmond, III et al. |
| 2004/0267213 A1 | 12/2004 | Knapp |
| 2005/0033403 A1* | 2/2005 | Ward ........................ A61F 2/95 623/1.11 |
| 2005/0222581 A1* | 10/2005 | Fischer .............. A61B 17/3421 606/108 |
| 2016/0324579 A1 | 11/2016 | Irby |
| 2018/0318114 A1* | 11/2018 | Huang ...................... A61F 2/86 |

OTHER PUBLICATIONS

Search Report and Written Opinion from corresponding International Patent Application No. PCT/US2020/62860, dated Mar. 4, 2021.

* cited by examiner

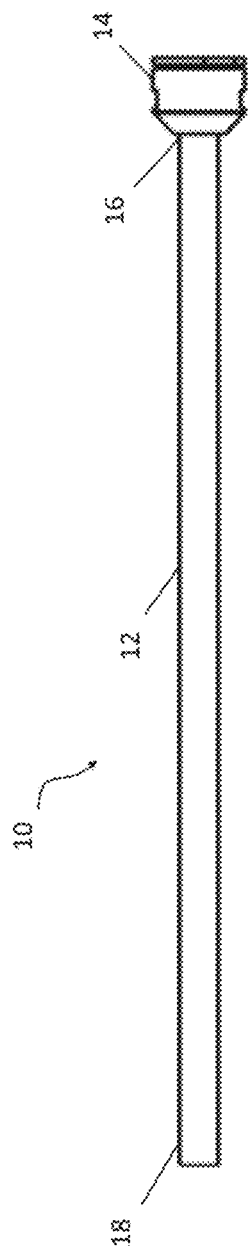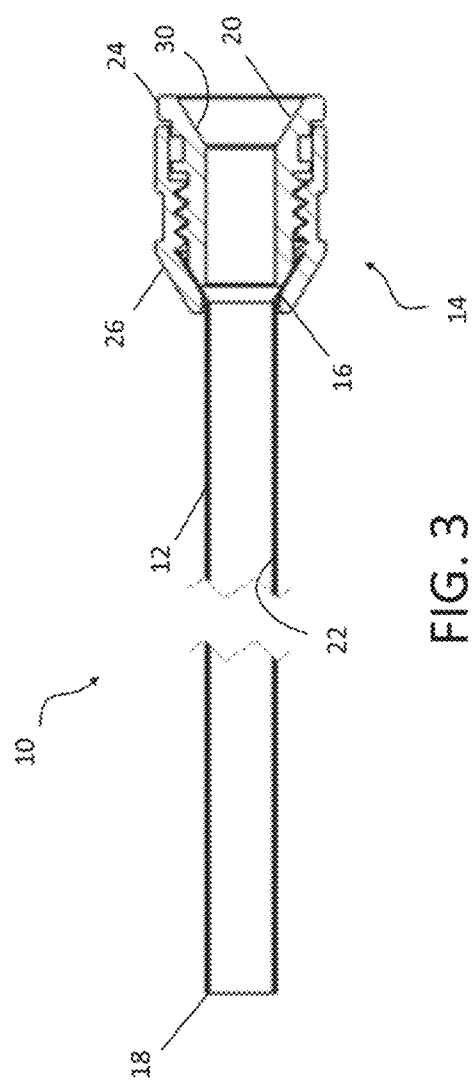

DEVICES FOR THE TREATMENT OF BENIGN PROSTATIC HYPERPLASIA AND RELATED LOWER URINARY TRACT SYMPTOMS

RELATED APPLICATIONS

This application claims priority to U.S. Provisional Application No. 62/943,112, filed Dec. 3, 2019. The priority of this application is expressly claimed, and the disclosure is hereby incorporated by reference in its entirety.

FIELD OF THE PRESENT DISCLOSURE

This disclosure relates to devices for managing or treating body tissues obstructing a hollow body lumen, such as the prostatic lobe tissues obstructing the urethra.

BACKGROUND

The prostate is a walnut-shaped gland that wraps around the urethra through which urine is expelled from the bladder and plays a crucial role in the reproductive system of men. Although the gland starts out small, it tends to enlarge as a man ages. An excessively enlarged prostate results in a disease known as benign prostatic hyperplasia (BPH). Benign prostatic hyperplasia (BPH) refers to the abnormal, but non-malignant (non-cancerous) growth of the prostate observed very commonly in aging men. BPH is a chronic condition and is associated with the development of urinary outflow obstruction or luminal narrowing in the prostatic urethra. Bladder outlet obstruction (BOO) refers to a blockage at the base of the bladder that reduces or stops the flow of urine into the urethra and may be secondary to BPH. A range of related disorders referred to collectively as Lower Urinary Tract Symptoms (LUTS) can result, including sexual dysfunction, frequent urination, difficulty in voiding urine, urinary retention, urinary leakage, and urinary tract and bladder infections that worsen as the abnormal growth in the prostate enlarges and progresses.

Surgical procedures provide BPH relief by removing a significant portion the prostate tissue. Several traditional surgical procedures are available, all of which require hospitalization and some form of spinal, epidural, or general anesthesia. Transurethral resection of the prostate (TURP) is the main surgical treatment for BPH and remains the gold standard against which other treatments are compared. Traditional surgical techniques differ in the location of the incision made by the surgeon to access the prostate and in the method by which prostatic tissue is removed. For example, some surgeries use laser energy, heat, or radio frequency to remove tissue from the prostate. They include laser enucleation, photoselective vaporization (PVP), transurethral needle ablation (TUNA) using radiofrequency energy, transurethral microwave thermotherapy (TUMT) and transurethral incision of prostate (TUIP). However, these traditional surgical approaches to the treatment of BPH are invasive, non-reversible, and have significant drawbacks including the placement of a temporary catheter for a few months, risk of infection, loss of sexual function, urinary incontinence, and restenosis—wherein recurring hyperplasia of cells in the prostate regrow to cause a recurrence of the narrowing of the urethra opening and also a recurrence of the LUTS symptoms described above.

Although removing prostatic tissue relieves some BPH symptoms, tissue removal by traditional surgical approaches is irreversible and any adverse effects of the surgery may afflict the patient for life or affect the patients' quality of life. Moreover, surgical approaches are associated with the inherent risks from the surgery itself, risk of recurrence from the regrowth of removed prostatic tissue, and, depending on the extent of the disease and the particular surgical approach necessary for an individual patient, can require recovery periods as long as 3 to 6 weeks.

Because of the recognized drawbacks of traditional surgery, less invasive therapies have been developed and, depending on the extent of disease, may be chosen by patients and their physicians as an alternative to lifelong medication or surgery. These less invasive therapies may be suited for those patients not willing or medically not fit to have a surgical procedure performed under general anesthesia. In addition, younger patients also prefer a less invasive, reversible treatment without compromising sexual function, and leave the option of receiving a permanent, non-reversible treatment affecting sexual function at a later age. Further, since less invasive therapies permit treatment in the office or clinic using a local anesthetic, benefits include patient's comfort and healthcare system economy as compared to treatments under general anesthesia in a hospital setting.

Less invasive techniques include transurethral methods that actually remove enlarged prostatic tissue that are generally less traumatic than traditional surgery, but each destroys prostatic tissue and is irreversible. To avoid destroying the prostatic tissue, other therapeutic procedures have been developed that are designed to enlarge the diameter of the prostatic urethra without actual removal of tissue from the prostate gland, such as by implanting a device within the prostatic urethra that is designed to enlarge the diameter of the urethra. A prostatic implant involves a procedure wherein the urologist inserts a small device within the prostatic urethra which is narrowed by enlarged prostatic tissue. Once in place, the implant is designed to expand and help keep the urethra open by pushing out the tissue lobes, while preventing enlarged prostate tissue from total impingement and opening of the urethra. Ideally, prostatic implants eliminate the need to surgically remove prostatic tissue and are expected to reduce the risks of infection, sexual dysfunction, and incontinence, inherent and traditional to even less-invasive, surgical approaches. The procedure may also be designed to be reversible since the implants may be removed and additional surgical treatments may be performed in the future.

Thus, office-based treatment of BPH/LUTS using flexible cystoscopes that are currently used to image the urinary tract, including the prostatic urethra, and diagnose BPH and related symptoms involve the placement of an implantable expander device in the prostatic urethra and mechanically retract the lobes, increase the urethra lumen and allow the passage of urine. The expander may be retrievable using commercially available cystoscopes, sheaths and graspers or other retrieval tools used in urology procedures. Accordingly, it would be desirable to provide a sheath having features configured to assist the retrieval of the implant from the prostatic urethra any time after implantation for given duration of time. The techniques of this disclosure satisfy these and other needs.

SUMMARY

This disclosure is directed to a sheath for retrieving an implant from a placement location in a lumen of a body. This disclosure is directed to a sheath for retrieving an implant from a placement location in a lumen of a body. The sheath may include an elongated shaft member having at least one lumen with an inner diameter, an atraumatic distal end and a proximal end. The shaft member has at least one region of modified flexibility. The distal end of the shaft member may be configured to compress the implant to a reduced profile.

In one aspect, a hub may be secured to the proximal end of the elongated shaft member and an opening in the hub that tapers from a proximal diameter greater than the inner diameter of the shaft member that is configured for advancement of a cystoscope through the at least one lumen of the shaft member.

In one aspect, the hub may have a proximal portion and a distal portion that thread together so that the proximal end of the shaft member is secured to the hub by compression. The proximal portion of the hub may have a frusto-conical projection that engages a flared portion of the proximal end of the shaft member.

In one aspect, the hub may be further configured to form a seal with a cystoscope inserted through the opening.

In one aspect, the hub may be further configured to releasably secure a cystoscope inserted through the opening.

In one aspect, the shaft member region of modified flexibility may be adjacent the distal end and have a reduced durometer value relative to proximal regions of the shaft member. The shaft member region adjacent the distal end may have a different material than the proximal regions of the shaft member.

In one aspect, the shaft member region of modified flexibility adjacent the distal end may be extremely flexible relative to the proximal and distal regions of the shaft member to allow complete articulation of a flexible cystoscope, when introduced through the sheath. The shaft member region of modified flexibility adjacent to the distal end may have a lower thickness or contain features that enhance flexibility. For example, the proximal and distal ends may be reinforced with a braided metallic wire and the region adjacent to the distal end may not be reinforced with metallic braid or reinforced with a lower density of braid (or low braid angle) to improve flexibility. Other features include and not limited to laser etching linear or spiral grooves in the shaft member region adjacent to the distal end to improve flexibility.

In one aspect, the shaft member may have a reinforcement configured to facilitate compression of an implant. The reinforcement may be at least one metallic band. This reinforcement may be of a very short length of a few millimeters generally between 1-15 mm, or more preferably between 2-5 mm.

In one aspect, the distal end of the shaft member may have a tapered edge. The tapered edge may angled inward toward the inner diameter so that the sheath follows the contours of the cystoscope during advancement through the urethra or other body lumens without causing trauma, injury or tissue damage and minimal pain to patients during the treatment procedure. The tapered edge of the sheath may be softer compared to the distal end to provide an atraumatic tip.

In one aspect, the distal end of the shaft member may be configured to seal with a cystoscope inserted through the shaft member.

In one aspect, the sheath may have multiple lumens. At least one lumen may be circumscribed within another lumen or at least one lumen may be adjacent another lumen.

In one aspect, the shaft member has an inner diameter ranging between 5 F-20 F and an outer diameter ranging between 8 F-26 F.

In one aspect, the implant may be a prostatic implant having an expandable profile configured to restore patency to a patient's urethra.

This disclosure also includes a method for retrieving or placing an implant from or at a placement location in a lumen of body. A sheath may be provided, wherein the sheath includes an elongated shaft member having at least one lumen with an inner diameter, an atraumatic distal end and a proximal end. The shaft member has at least one shaft member region of modified flexibility. A cystoscope may be introduced through at least one lumen of the shaft member. The sheath and cystoscope may be advanced through the lumen of the body. The implant may be retrieved or released via relative movement with the sheath.

In one aspect, the implant may be secured against relative movement with the sheath. The implant may be compressed to a reduced profile within the sheath. Consequently, the sheath, the cystoscope and the compressed implant may then be withdrawn from the lumen of the body.

In one aspect, the cystoscope may be releasably secured to the sheath prior to advancing the sheath and cystoscope through the lumen of the body.

In one aspect, compression of the implant may be confirmed by visualization.

In one aspect, the implant may be secured against relative movement with the sheath by a grasper.

This disclosure also includes a sheath for introducing a cystoscope and a delivery catheter containing an implant for placement in a lumen of a body. The sheath may have an elongated shaft member having two or more lumens each with an inner diameter, an atraumatic distal end and a proximal end, a hub secured to the proximal end of the elongated shaft member and two or more openings in the hub that each taper from a greater proximal diameter and are configured for advancement of a cystoscope through one lumen of the shaft member and a delivery catheter through another lumen of the shaft member.

Still further, this disclosure also includes a method for placement of an implant in a lumen of body. The method may involve providing a sheath including an elongated shaft member, a hub secured to the proximal end of the elongated shaft member, and at least two openings in the hub that each taper from a greater proximal diameter. A cystoscope may be introduced through one opening and at least one lumen of the shaft member. A delivery catheter containing an implant may be advanced through another lumen of the shaft member until the delivery catheter is visualized. The cystoscope may be secured against relative movement with the sheath. The implant may be released at a target location within the body lumen. The sheath, the cystoscope and the delivery system may be withdrawn from the lumen of the body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 2 schematically depicts a side view of an implant retrieval sheath according to an embodiment.

FIG. 3 schematically depicts a sectional view of the implant retrieval sheath according to an embodiment.

DETAILED DESCRIPTION

Figure 1:
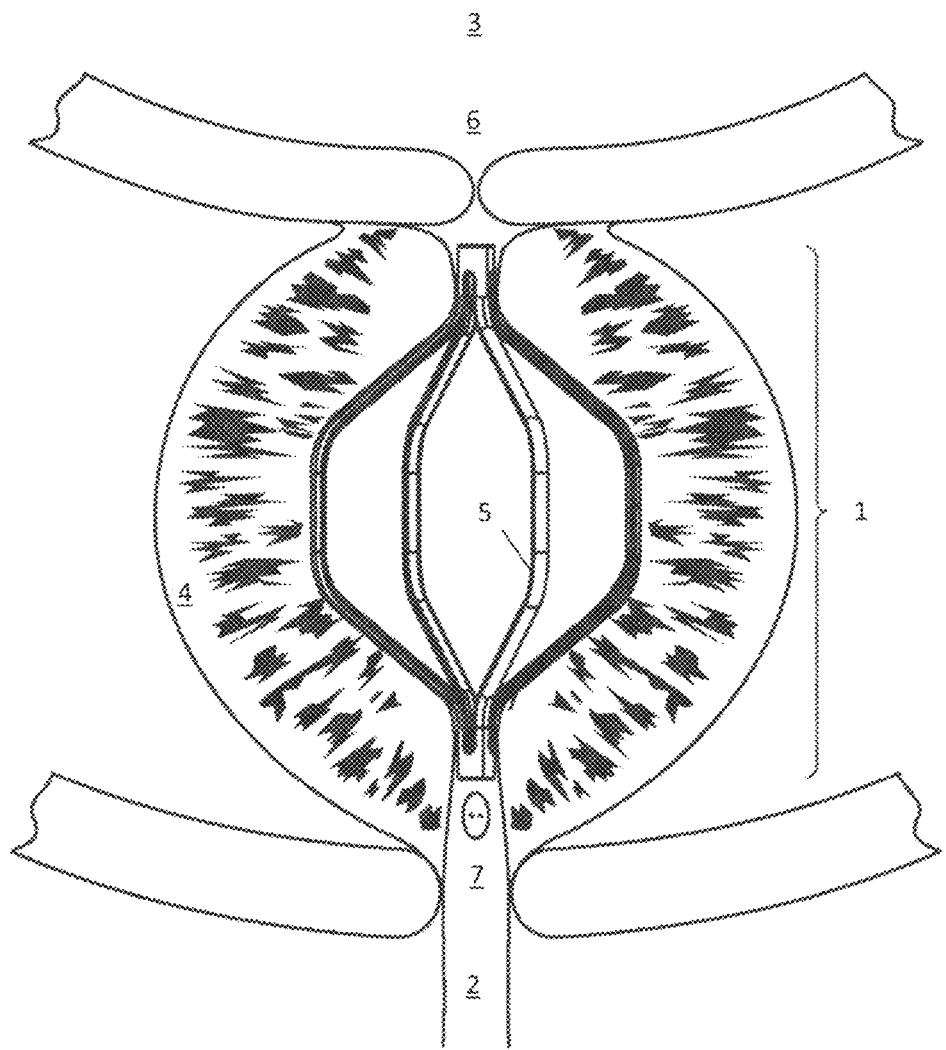
FIG. 1 is a cross-section of the male anatomy comprising the lower portion of the bladder, and the prostatic urethra in a physiological configuration typical of a patient suffering from BPH, showing placement of an implant that may be disposed using the devices and systems of this disclosure in the prostatic urethra and engaging prostatic tissue on either side thereof between the bladder neck opening and the verumontanum according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Moreover, as used in this specification and the appended claims, the singular forms "a," "an" and "the" include plural referents unless the content clearly dictates otherwise.

Definitions: The terms "therapeutically effective displacement" or "therapeutically effective retraction" or "therapeutically effective expansion", are used interchangeably herein and refer to an amount of displacement of prostatic tissue proximate to a restricted area of a urethra sufficient to increase the urethral lumen and treat, ameliorate, or prevent the symptoms of benign prostatic hyperplasia (BPH) or comorbid diseases or conditions, including lower urinary tract symptoms (LUTS), bladder outlet obstruction (BOO), benign prostatic obstruction (BPO), wherein the displacement of prostatic tissues exhibits a detectable therapeutic, prophylactic, or inhibitory effect. The effect can be detected by, for example, an improvement in clinical condition, or reduction in symptoms or absence of co-morbidities. Examples of clinical measures include a decrease in the international prostate symptom score (IPSS), reduction in post-void residual (PVR) volume of urine in the bladder after relief or increase in the maximum urinary flow rate (Qmax) or improvement in quality of life (QoL), improvement in sexual health (sexual health inventory for men or SHIM score, men's sexual health questionnaire or MSHQ score) after treatment. The precise distance or volume of the displacement of prostatic tissue will depend upon the subject's body weight, size, and health; the nature and extent of the enlarged or diseased prostatic condition and the size of the implant selected for placement in the patient.

As used herein, a patient "in need of treatment for BPH" is a patient who would benefit from a reduction in the presence of or resulting symptoms of enlarged prostatic tissue caused by a non-malignant enlarging of the prostate gland and related disorders, including LUTS, urinary outflow obstruction symptoms and luminal narrowing of the prostatic urethra. As used herein, the terms "implant" or "expander" or "device" refer to the prosthetic device that is implanted within the prostatic urethra to relieve LUTS associated or caused by BPH.

As used herein, the terms "tissue engaging" with regard to arms, struts or other extensions of the structure of the implant refers to a length of the physical structure of the implant that engages prostatic tissue along the main portion of the lobes of the organ compressing on the urethra and restraints the tissue from further impingement on the patency of the urethra. "Tissue retracting" refers to the ability of the structure of the implant to exert the requisite force to displace tissue away from the compressed or narrowed urethra. The requisite force could be supplied by the inherent structure of the implant or by the expansion of the implant from the compressed to the expanded configuration, particularly where the implant is fabricated from a shape-memory or super-elastic material having a predetermined expanded configuration designed to engage the hyperplasic prostate tissue and exert the requisite tissue retraction force. The length of a tissue-engaging or tissue-retracting structural feature in contact within these definitions is spaced away from the intra-lobular grooves that run along the length of the prostate surrounding the urethra and requires contact with a length of tissue along the length of the two lateral or lateral and medial lobes.

With respect to orientation of the various structures and anatomical references described herein, the term "proximal" and "distal" are relative to the perspective of the medical professional, such as an urologist, who is manipulating the delivery system of the disclosure to deploy the implants described herein. Accordingly, those features of the delivery system held by the hand of the urologist are at the "proximal" end and the assembled system and the implant, initially in its compressed configuration, is located at the "distal" end of the delivery system.

Referring to FIG. 1, a cross-section of the male anatomy shows the prostate gland 1 surrounding the urethra 2. The urethra 2, under normal conditions, provides fluid communication from urine stored in the bladder 3 to be expelled from the body under voluntary muscular control of the external urethral sphincter. Normal or "true" prostate tissue 4 surrounds the urethra 2 and, in the absence of disease, does not impinge on the patency of the urethra 2. In patients suffering from benign prostatic hyperplasia (BPH), the urethra 2 is narrowed by hyperplasic tissue, i.e. prostate tissue 4 that exhibits excess growth towards the urethra 2. This excess of non-cancerous cellular growth leads to the symptoms of BPH described above, including, lower urinary tract symptoms (LUTS) and urinary outflow obstruction, and urinary incontinence. In FIG. 1, an implant 5 delivered using the devices and systems of this disclosure is shown engaging prostate tissue 4 along a length of the implant 5 to restore the patency of the urethra 2 and to permit unimpeded urine flow from the bladder 3. The selective placement of the implant 5 at a target site, between bladder neck opening 6 and verumontanum 7, as shown is an important characteristic so that implant 5 does not puncture, perforate or incise the surrounding tissue. The implant 5 is designed to remain in place within the prostatic urethra 2. The implant 5 does not extend into the urinary bladder 3, where the structural material of the implant 5 could become encrusted or otherwise degraded from constant exposure to urine causing complications and making retrieval more difficult, and the implant 5 does not interfere with the voluntary control of the external urethral sphincter or interfere with sexual functions.

An implant 5 according to the techniques of this disclosure has a plurality of tissue-engaging structures to exert a force against enlarged prostate tissue 4 proximate to the urethra 2. As described below, the number of the plurality of tissue-engaging structures can be 2, 4, or greater than 4 tissue-engaging extensions, such as struts or arms. The use of 3 extensions is avoided when the three extensions are oriented to each fit within the intralobular grooves of the prostate 4. Accordingly, any plurality of tissue engaging structures is a possibility as long as the structure is oriented asymmetrically to ensure that the implant 5 is oriented outside the 3 intralobular grooves formed by the length of tissue contact between the 2 lateral and one medial lobes. Embodiments using three tissue-engaging structures may be used to treat anatomies when the urethral anatomy consists of bilateral lobes and the third lobe is not involved with urethral narrowing.

The implants 5 may be fabricated from shape memory materials, alloys, spring materials, and super elastic materials including Nitinol (nickel-titanium alloy), Nitinol-based alloys, cobalt chromium alloys, spring steels, and spring stainless steels. Other known shape memory materials include poly-ether-ether-ketone (PEEK), and shape memory and bio-absorbable polymers and metals (polylactic acid, polyglycolic acid and their copolymers; magnesium alloys). The above materials may be coated with thin film coatings to prevent encrustation, corrosion and stone formation. Coatings may include ceramic materials like alumina, silicon carbide, silicon nitride and zirconia and other ceramic coatings that are inert to urine and prevent encrustation, stone formation and to prevent the deterioration of the material forming the implant in the chemical or urine environment. Coatings may also be polymers such as polytetrafluoroethylene (PTFE), Parylene, silver and other antimicrobial coatings, silicone derivatives, and other similar materials recognized by those of ordinary skill in the art.

The implant 5 may also include therapeutic coatings adhered to the surface of the implant 5 for controlled drug release following implantation in the prostatic urethra 2 in the manner known for drug-eluting implants to reduce hyperplasia and tissue proliferation. The coatings contain pharmaceutically active anti-inflammatory drugs and anti-proliferative agents including sirolimus, novolimus, everolimus, biolimus, zotarolimus, paclitaxel and others that are used to prevent restenosis.

Implants 5 may also be coated with drugs to treat BPH symptoms. Such embodiments have the advantage of using high locally high tissue doses in the diseased prostatic regions of the urethra 2 for greater effectiveness to relax smooth muscle cells, reduce tissue proliferation and size of the prostate 4 without incurring the side effects from drugs circulating in other parts of the body. Potential drug candidates include alpha-adrenergic blockers like, alfuzosin, doxazosin, tamsulosin, terazosin and silodosin. Other drug candidates include 5-alpha-reductase inhibitors like, dutasteride and finasteride, and anticholinergic agents. Other drug candidates are anti-cholinergic agents like, oxybutynin, fesoterodine, darifenacin, tolterodine tartrate, tolterodine, solifenacin. A combination of drugs may also be coated on the surface, including alpha blocker+5-alpha-reductase inhibitor or alpha blocker+anticholinergic agents. In addition, anti-infective agents or antimicrobial agents or antibiotics like fluoroquinolones (e.g., ciprofloxacin) macrolides, tetracyclines, and trimethoprim.

Typically, the drugs are mixed with solvents and polymers into solution and spray coated on the outer surface of the implant 5 to achieve the desired drug release characteristics. The manufacturing processes are similar to those used for drug eluting stents used to treat coronary artery disease. Often, the coating may be on the abluminal side to ensure more effective drug release and deposition into the urethral tissue of the prostatic urethra 2 and minimize washout during urine outflow. The drugs may also be deposited in micro-reservoirs or micro-depots on the outer surface of the implant 5 to load the drug and covered by a polymeric coating to controllably elute drug into the urethral tissue. Typical polymers used to load the drugs are polylactic acid (PLA), poly-L-lactic acid (PLLA) polyglycolic acid (PGA), and their copolymers; polyurethanes; poly(methyl methacrylate) (PMMA) or poly(n-butyl methacrylate) (PBMA); and their combinations thereof. Other polymers and solvents may be used by those skilled in the art to load sufficient drug and maintain coating integrity with the implant surface. Multiple layers of coatings may be used to achieve the desired drug loading and controlled release characteristics.

The implant 5 for restoring patency of the urethra 2 can be removed after implantation by employing a sheath 10, a grasper and a cystoscope (not shown) according to the techniques of this disclosure, such as retrieval sheath 10 as shown in FIG. 2. In this exemplary embodiment, sheath 10 includes an elongated tubular shaft member 12 having hub 14 at proximal end 16 and distal end 18. During retrieval, relative movement between sheath 10 and implant 5 (not shown in this view) causes the implant 5 to be compressed inside sheath 10 allowing its removal from the patient. As will be appreciated, the relative movement can result from distal movement of sheath 10 while implant 5 is held relatively stationary by a grasper, from a proximal movement of implant 5 being pulled by a grasper while sheath 10 is held relatively stationary, or from some combination of these movements.

To further aid the description of this embodiment, FIG. 3 is a cross-sectional view showing details of hub 14 and proximal shaft end 16. As depicted, hub 14 features a beveled opening 20 with a relatively greater proximal diameter that tapers to a relatively smaller distal diameter that corresponds to the inner diameter of shaft member 12. As will be appreciated, the relatively greater proximal diameter of opening 20 facilitates insertion of a cystoscope that may be advanced through lumen 22 of shaft member 12. Hub 14 is characterized by a frusto-conical proximal portion 24 that is engaged by screw threads with distal portion 26 that cooperatively compress a flared end of proximal end 16 of shaft 12 against frusto-conical proximal portion 24 to form a sealing connection. As desired, an adhesive or other similar technique may additionally be employed to augment bonding between shaft 12 and hub 14.

Figure 4:
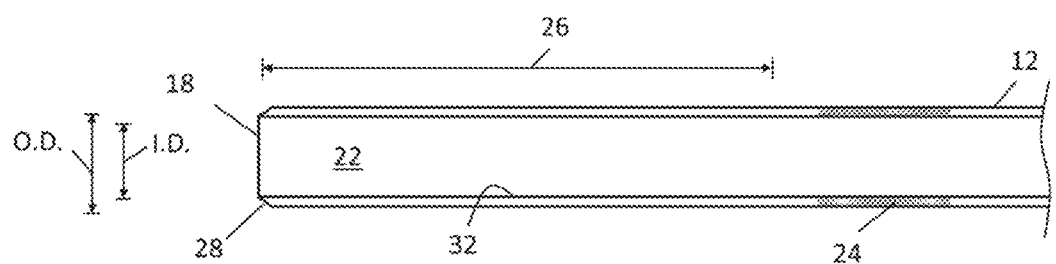
FIG. 4 schematically depicts a detail view of a distal end of the implant retrieval sheath according to an embodiment.

Further, FIG. 4 schematically depicts a detail view of distal end 18 of shaft 12. To facilitate retrieval of implant 5, distal end 18 is configured to have sufficient column strength to collapse the implant 5 while it is being pulled into it using a grasper. Moreover, distal end 18 is configured to allow steerability and/or articulation of a flexible cystoscope advanced through lumen 22 while reducing or minimizing anatomical trauma. To enable this, sheath 10 may be designed to include one, all, or a combination of the following features. Distal tip 18 may utilize a different durometer polymer material than the main shaft 12. Distal end 18 may be reinforced with one or more metallic rings 24, (one of ordinary skill in the art will appreciate that braid, coil, and other configurations may also be used to provide the desired reinforcement) to provide additional resistance to radial expansion and/or column strength thereby aiding collapse of implant 5 when pulled into sheath 10. In such embodiments, metallic ring(s) 24 may be made of stronger and stiffer (high elastic modulus) materials like stainless steel, titanium, titanium alloys, cobalt-chromium alloys or other biocompatible metals and alloys commonly used in medical devices. Further, distal end 18 may feature a region 26 not supported by metallic reinforcement. The intermediate region 26 has modified flexibility and may be fabricated using a different (softer, low modulus) material (like medical polymers or extrusions commonly used in medical devices) or a material with low durometer to demonstrate greater flexibility compared to the distal end 18 and proximal end 12. Region 26 may also have a lower wall thickness compared to the rest of the sheath 10. It may also contain other features that enhance flexibility, such as linear or spiral grooves, without compromising the structural integrity of the sheath. Such extreme flexibility in region 26 will not significantly limit the range of articulation, steerability or movement of a flexible cystoscope, when inserted through the sheath 10. The softer region may be 1-50 mm long, such as, 2.5-7.5 mm long. Still further, distal end 18 may have a tip with a tapered edge 28, creating a smoother transition between a cystoscope advanced through inner lumen 22 and an outer diameter of shaft member 12. The tapered edge 28 may be tapered inward so that the sheath tip does not flex outward during advancement of the sheath, along with a cystoscope inside the sheath 10, into tortuous (or non-linear) urethra lumens (or other body lumens) and cause trauma and injury to tissue. In addition, such a configuration minimizes pain when the sheath 10 and cystoscope are advanced through the prostatic urethra 2 under local anesthesia, facilitating treatment in an office or clinic, without the need for general anesthesia. In other embodiments the edge may also be rounded to prevent trauma or injury to tissue during advancement in bodily lumens. Moreover, distal end 12 may be configured to seal over the cystoscope as it is advanced through lumen 22. To accomplish this, at least a portion of distal end 18 may be formed from the same material as the rest of shaft member 12, or as warranted, with a more elastic material, including but not limited to polyurethane, silicone, etc.

An optional aspect of hub 14 is the inclusion of silicone, rubber, or other elastomer material 30 (FIG. 3) to facilitate creating a seal between a cystoscope advanced through lumen 22 and sheath 10 to reduce backflow of bodily fluids. The seal may or may not require additional user input or step to enable a complete seal. In one embodiment, the seal is shaped and undersized such that the insertion of the cystoscope will automatically form a seal between the sheath 10 and the cystoscope. In another embodiment, the hub 14 may be rotated, pushed, or interacted with to manually close the seal over the cystoscope. In such embodiment, the seal also secures the position of the sheath 10 relative to the cystoscope during the expander device retrieval. This facilitates the advancement of the cystoscope and sheath 10 as a system (no relative sliding) without impacting the steerability of flexible cystoscope, during sheath 10 advancement, grasper advancement and grasping implant 5. Once the implant 5 is securely held, hub 14 may be loosened to allow relative advancement of shaft member 12 over implant 5 to collapse the implant 5 into lumen 22 of shaft member 12. Once implant 5 is inside shaft member 12, hub 14 can be re-tightened to securely attach shaft member 12 to the inserted cystoscope. The system can be easily retrieved, with no relative motion between the sheath 10 and cystoscope, without damaging the cystoscope and the urethra 2 wall.

Shaft member 12 and hub 14 have openings configured to allow the insertion of cystoscopes or other endoscopic instruments to visualize anatomical features and assist treatment. The inner diameter of shaft member 12 (indicated schematically on FIG. 4) can range between 5-22 Fr, or more preferably between, 8-18 F, to allow the passage of instruments with different diameters. The outer diameter shaft member 12 (also indicated schematically on FIG. 4) is designed to be as small as possible to minimize trauma to the anatomical passages, yet strong enough to allow advancement of instruments, and can range between 5-25 Fr, or more preferably between, 9-21 F. As one non-limiting example, sheath 10 may have a 20 F inner diameter with 24 F outer diameter. The overall length of sheath 10 is sufficient to reach the location of implant 5 within the prostate 4 through the patient's urethra 2 and may be approximately 32 cm, for example. The overall length can range between 20-50 cm depending on the patient anatomy and the length of different cystoscopes used during treatment procedure. Similarly, hub 14 has opening 20 to allow the insertion of cystoscopes or other endoscopic instruments to visualize anatomical features and assist treatment. The inner diameters of the hub 14 can range between 5-22 Fr, or more preferably between, 8-18 F, to allow the passage of instruments with different diameters. The outer diameter of the hub 14 is designed to be ergonomic for the user and can range between 2-50 mm, or more preferably between, 10-20 mm.

Shaft member 12 is desirably thin, flexible, soft, and yet strong enough to facilitate advancement without kinking. In one embodiment, shaft member 12 is formed from a reinforced polymer extrusion. For example, the polymer extrusion may be made with materials such as PEBA (Polyether Block Amide), Polytetrafluoroethylene (PTFE), etc. The extrusion may also be a multilayer construction using different polymers or the same polymer but with differing hardness. The reinforcement may be metallic, such as stainless steel, nitinol, etc., or a polymer, such as PEEK (Poly-Ether-Ether-Ketone), Nylon, etc. The reinforcement may be arranged in a coil or braided pattern and may not necessarily extend across the entire length of the sheath 10. Alternatively, shaft member 12 may be constructed from extruded polymers alone. Sheath 10 may also feature liner 32 (FIG. 4) along the inner diameter to help facilitate advancement of the cystoscope or other instruments by reducing friction. The liner may be made of PTFE, Nylon, or other materials with low coefficients of friction. Sheath 10 may also be coated with additional lubricious or hydrophilic material on the outer diameter to help facilitate advancement through the urinary tract. Suitable wall thicknesses for sheath 10 are 0.001-0.025", or more preferably 0.003-0.015". As noted above, hub 14 provides beveled opening 20 to facilitate introduction of a cystoscope or other instrument and also functions as a handle for the user to hold and manipulate sheath 10 during implant 5 retrieval. Hub 14 can be constructed from polycarbonate plastic or other suitable materials, including most thermoplastic polymers or metals.

In other embodiments, a sheath 10 according to the techniques of this disclosure may employ a shaft 12 having multiple lumens. One example is schematically depicted in the cross section of FIG. 5, which shows shaft member 12 with two adjacent lumens 34 and 36. The inner diameters of lumens 34 and 36 may have different inner diameters as shown to accommodate cystoscopes and other ancillary devices, or may have the same diameter in alternative embodiments. Another example of a multiple lumen sheath 10 is schematically depicted in FIG. 6, showing shaft member 12 with first lumen 38 and second lumen 40 defined within first lumen 38 by inner tubular member 42. Shaft member 12 and inner tubular member 42 may share a common portion of their respective circumferences so that second lumen 40 is circumscribed within first lumen 38, having a crescent-shaped configuration as shown. Alternatively, inner tubular member 42 may be coaxially disposed within shaft member 12 to form a concentric lumen. As will be appreciated, in any of these alternative embodiments the shapes and dimensions of the multiple lumens may be configured to optimize their respective inner dimensions within the constraint of the overall cross sectional area of shaft member 12 and tailor them to different cystoscope or other instrument profiles. The shaft member 12 may be made from a multi-lumen extrusion, with two or more lumens. The separate lumens allow advancement of the cystoscope, grasper and other instruments or irrigation through the lumens. Such embodiments feature a reduced outer diameter, or profile, to minimize patient discomfort and trauma during device introduction and treatment.

Figure 5:
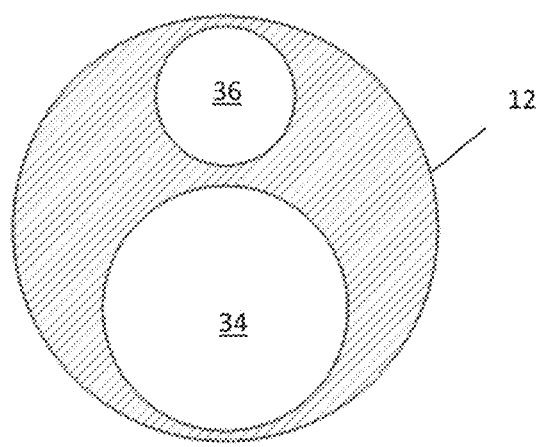
FIG. 5 schematically depicts a cross section of a multiple lumen embodiment of the implant retrieval sheath according to an embodiment.
Figure 6:
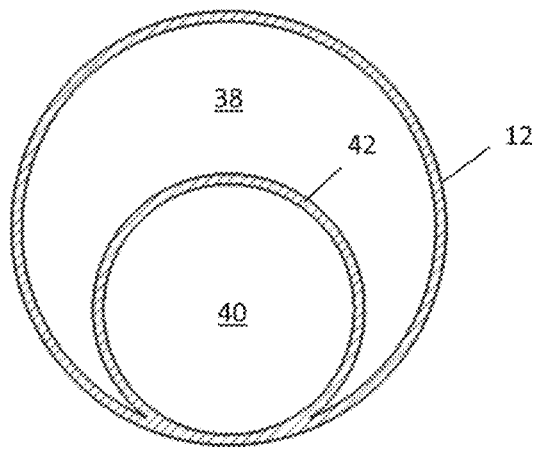
FIG. 6 schematically depicts a cross section of an alternative multiple lumen embodiment of the implant retrieval sheath according to an embodiment.

As will be appreciated by those skilled in the art, sheaths with multiple lumens described in FIG. 5 and FIG. 6 will require also different hubs with multiple lumens, sizes (lengths and diameters) and shapes to accommodate the introduction of different types of cystoscopes (disposable and/or reusable digital video cystoscopes and/or fiber-scopes—flexible and rigid) and other ancillary devices or instruments (graspers—flexible and rigid) during medical procedures.

In addition, such sheaths 10 may not only be used for the retrieval of implants 5 but also for the placement of implants 5 using cystoscopes. For example, one of the lumens may be used to introduce the cystoscope and another lumen may be used to introduce the delivery catheter with an implant 5 to deploy it at the target location. The length of the sheath 10, number of lumens and size of the lumens may be optimized for specific instruments used for medical treatment. Typically inner diameters of the lumen 34 to introduce 5 F-18 F outer diameter cystoscopes range between 6 F-20 F, and inner diameters of the lumen 36 to introduce the 5 F-12 F outer diameter delivery catheter range between 6 F-14 F. Typical lengths of sheaths 10 range between 20-50 cm depending on the type of cystoscope used during the medical procedure. Similarly lumens 38 and 40 may also be designed and optimized to introduce various medical instruments into body lumens using the lowest profile sheath 10 to minimize trauma and injury. One can also select different materials (differing in strength and elastic modulus or durometer; reinforced with braided wire or unreinforced), dimensions (thickness) for the proximal, mid and distal portion of the sheath 10 and the hub 14 to achieve desired properties. In some embodiments, the hub 14 may incorporate an irrigation port for saline irrigation to facilitate imaging during the medical procedure.

Figure 7:
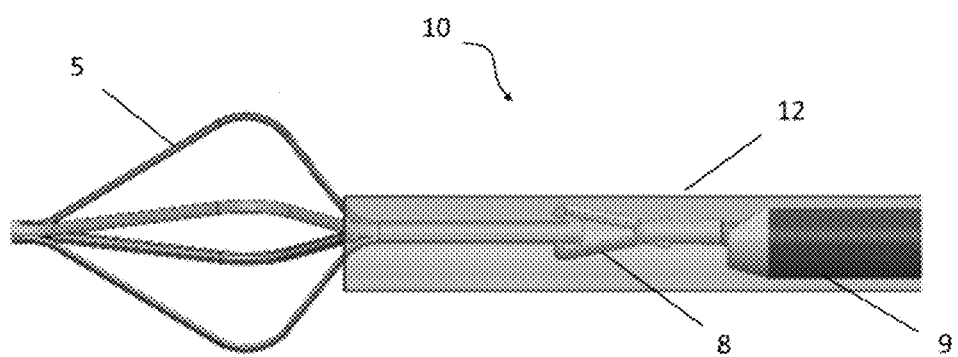
FIG. 7 schematically depicts a sheath with a grasper advanced through a cystoscope to engage an implant according to an embodiment.

A subject diagnosed for BPH/LUTS may be treated using an implant 5 to open the lumen obstructing lobes in the prostatic urethra 2. The implant 5 is placed between the bladder neck 6 and the verumontanum 7 for a given period of time between 30 days for up to a few (1-5) 3 years. Whenever desired, the implant 5 may be retrieved using a retrieval sheath according to the techniques of this disclosure. One exemplary routine involves inserting a flexible cystoscope is inserted into sheath 10 through beveled opening 20 of hub 14 so that sheath 10 does not prevent the articulation of the flexible cystoscope. Notably, the flexible cystoscope may be advanced through hub 14 and shaft member 12 of sheath 10 until the cystoscope exits the distal end 18. In one embodiment, the distal end of the cystoscope tip should be about 2-5 cm beyond the tip at distal end 18 of sheath 10, while confirming steerability of the cystoscope. In embodiments featuring a hub 14 that seals or attaches to the cystoscope, the appropriate manipulation can be performed to secure the cystoscope and sheath 10 together. Next, the cystoscope and sheath 10 are inserted into the patient's urethra 2, as a system, up to the location of implant 5 until implant 5 (or other target device) is visible. As schematically indicated in FIG. 7, grasper 8 is inserted through the working channel of cystoscope 9 and manipulated to hold or secure implant 5 in place. Once implant 5 is firmly grasped, retrieval sheath 10 is advanced forward (distally) over the cystoscope 9, gradually causing the collapse of implant 5 into a small profile at distal end 18 as it is drawn within sheath 10, under direct visualization of the cystoscope 9. As noted above, grasper 8 can also be used to pull implant 5 proximally within sheath 10, such as by retracting grasper 8 and cystoscope 9 simultaneously, or a combination of these movements may be employed so that the necessary relative motion occurs. Implant 5 compresses or collapses to a lower profile, as sheath 10 is forced or advanced over it. Visual confirmation that implant 5 is sufficiently compressed within sheath 10 may be obtained when the distal edge of implant 5 is only barely visible with cystoscope 9. Once implant 5 is inside sheath 10, the retrieval sheath 10, cystoscope 9 and grasper 8 are simultaneously removed from the urinary tract.

Correspondingly, it will be appreciated from the above disclosure that a sheath according to these techniques can be used at any point after placement of implant 5, such as immediately after implantation or after any given period of duration. As will be described in further detail, the present disclosure describes a sheath 10 that fulfills multiple performance requirements, including any or all of the following characteristics. The sheath 10 may be atraumatic to the urethra 2 and surrounding anatomical structures inside the body during advancement and retraction of the sheath 10 through the urinary system. The sheath 10 may facilitate retrieval of implant 5 under direct visualization of commercially available flexible cystoscopes 9 with the aid of commercially available graspers 8, such as laparoscopic forceps or the like. The tip of the sheath 10 may be sufficient strong with respect to radial expansion and column strength to collapse implant 5 to a smaller profile without kinking when implant 5 is pulled within the sheath 10. The sheath 10 may be able to hold the implant 5 in a constrained (compressed to a low-profile, or small diameter) configuration, such as one that is less than 18 F, after the implant 5 is disposed within the sheath 10. The sheath 10 is configured to cause minimal pain or bleeding during use, and to minimize discomfort to the patient. The sheath 10 is configured to have sufficient length to reach the target site, which includes the prostatic urethra 2 and the urinary bladder 3. The sheath 10 is configured to be compatible with all commercially-used flexible cystoscope lengths, such as approximately 40-60 cm. The sheath 10 is configured to be soft and flexible enough to easily navigate the tortuosity of the urethra 2 from the penis to the urinary bladder 3. The sheath 10 is configured to be flexible enough so that it does not significantly impede the cystoscope's steerability at the distal end, and able to visualize the anatomical features and landmarks (external sphincter, verumontanum, bladder neck and urinary bladder) during advancement and deployment. The sheath 10 may also be configured to secure/lock the sheath 10 on the cystoscope 9 during advancement and after the implant 5 has been compressed within the sheath 10. The sheath 10 may also be configured to enable use by a single operator, using a flexible cystoscope 9 and a grasper 8, for retrieval of the implant 5 without the need for an assistant.

Notably, conventionally-available devices are not configured for use in the above manner with flexible cystoscopes to retrieve prostatic implants. Existing sheaths that are smaller in diameter cannot accommodate 17 F cystoscopes, while larger sheaths are stiff and can damage the urethra during advancement through the tortuous prostatic urethra and cause patient discomfort and pain. In addition, conventional sheaths typically have a very tight valve that makes insertion of the scope though the sheath or alternatively, advancement of the sheath over the cystoscope very difficult, despite the use of medical grade lubricating agents.

The exemplary embodiments disclosed above are merely intended to illustrate the various utilities of this disclosure. It is understood that numerous modifications, variations and combinations of functional elements and features of the present disclosure are possible in light of the above teachings and, therefore, within the scope of the appended claims, the present disclosure may be practiced otherwise than as particularly disclosed and the principles of this disclosure can be extended easily with appropriate modifications to other applications.

All patents and publications are herein incorporated for reference to the same extent as if each individual publication was specifically and individually indicated to be incorporated by reference. It should be understood that although the present disclosure has been specifically disclosed by preferred embodiments and optional features, modification and variation of the concepts herein disclosed may be resorted by those skilled in the art, and that such modifications and variations are considered to be within the scope of this disclosure.

What is claimed is:

1. A sheath for retrieving or placing an implant from or at a placement location in a lumen of a body, comprising:
   an elongated shaft member with at least one shaft member region of modified flexibility having at least one lumen with an inner diameter configured for advancement of a cystoscope therethrough, an atraumatic distal end and a proximal end having a tubular portion, a flared portion having an inner surface and an outer surface, the atraumatic distal end being positioned opposite to the proximal end and configured to compress the implant to a reduced profile; and
   a hub secured to the outside surface of the proximal end of the elongated shaft member, the hub having an opening that tapers from a proximal diameter greater than the inner diameter of the shaft member, and comprising: i) a proximal portion having a cylindrical portion and a frusto-conical projection such that the cylindrical portion is configured to correspond to the inner diameter of the tubular portion of the proximal end of the elongated shaft member and the frusto-conical projection is configured to engage the inner surface of the flared portion of the proximal end of the elongated shaft member, and ii) a distal portion that is configured to engage the outer surface of the flared portion of the proximal end of the elongated shaft member and thread together with the proximal portion to cooperatively compress and secure the flared and tubular portions of the proximal end of the shaft member to form a sealing connection.

2. The sheath of claim 1, wherein the hub is further configured to form a seal with a cystoscope inserted through the opening.

3. The sheath of claim 1, wherein the hub is further configured to releasably secure a cystoscope inserted through the opening.

4. The sheath of claim 1, wherein the shaft member region of modified flexibility is adjacent the atraumatic distal end and has a reduced durometer value relative to proximal regions of the shaft member.

5. The sheath of claim 4, wherein the shaft member region adjacent the atraumatic distal end comprises a different material than the proximal regions of the shaft member.

6. The sheath of claim 1, further comprising a reinforcement configured to facilitate compression of an implant.

7. The sheath of claim 6, wherein the reinforcement comprises at least one metallic band.

8. The sheath of claim 1, wherein the atraumatic distal end of the shaft member has a tapered edge.

9. The sheath of claim 1, wherein the atraumatic distal end of the shaft member is configured to seal with a cystoscope inserted through the shaft member.

10. The sheath of claim 1, wherein the sheath comprises multiple lumens.

11. The sheath of claim 10, wherein at least one lumen is circumscribed within another lumen.

12. The sheath of claim 10, wherein at least one lumen is adjacent another lumen.

13. The sheath of claim 1, wherein the shaft member has an inner diameter ranging between 5 F-20 F and an outer diameter ranging between 8 F-26 F.

14. The sheath of claim 1, wherein the implant is a prostatic implant having an expandable profile configured to restore patency to a patient's urethra.

15. A method for retrieving or placing an implant from or at a placement location in a lumen of body, comprising:
   providing a sheath having an elongated shaft member comprising at least one shaft member region of modified flexibility, an atraumatic distal end and a proximal end having a tubular portion, a flared portion having an inner surface and an outer surface, the atraumatic distal end being positioned opposite to the proximal end and configured to compress the implant to a reduced profile, the sheath further comprising a hub secured to the outside surface of the proximal end of the elongated shaft member, the hub having an opening that tapers from a proximal diameter greater than the inner diameter of the shaft member, and comprising: i) a proximal portion having a cylindrical portion and a frusto-conical projection such that the cylindrical portion is configured to correspond to the inner diameter of the tubular portion of the proximal end of the elongated shaft member and the frusto-conical projection is configured to engage the inner surface of the flared portion of the proximal end of the elongated shaft member, and ii) a distal portion that is configured to engage the outer surface of the flared portion of the proximal end of the elongated shaft member and thread together with the proximal portion to cooperatively compress and secure the flared and tubular portions of the proximal end of the shaft member to form a sealing connection;

introducing a cystoscope through at least one lumen of the shaft member;

advancing the sheath and cystoscope through the lumen of the body; and retrieving or releasing the implant via relative movement with the sheath.

16. The method of claim 15, wherein the step of retrieving the implant comprises securing the implant against relative movement with the sheath, compressing the implant to a reduced profile within the sheath, and withdrawing the sheath, the cystoscopy and the compressed implant from the lumen of the body.

17. The method of claim 15, further comprising releasably securing the cystoscope to the sheath prior to advancing the sheath and cystoscope through the lumen of the body.

18. The method of claim 16, further comprising confirming compression of the implant by visualization.

19. The method of claim 16, wherein the implant is secured against relative movement with the sheath by a grasper.

* * * * *